US008066992B2

(12) United States Patent
Epshtein

(10) Patent No.: US 8,066,992 B2
(45) Date of Patent: Nov. 29, 2011

(54) MEDICAMENT AND A METHOD OF TREATING A PATHOLOGICAL SYNDROME

(76) Inventor: Oleg Iliich Epshtein, Moscow (RU)

(*) Notice: Subject to any disclaimer, the term of this patent is extended or adjusted under 35 U.S.C. 154(b) by 0 days.

(21) Appl. No.: 12/495,104

(22) Filed: Jun. 30, 2009

(65) Prior Publication Data

US 2009/0285781 A1    Nov. 19, 2009

Related U.S. Application Data

(62) Division of application No. 10/522,652, filed as application No. PCT/RU02/00369 on Feb. 8, 2002, now Pat. No. 7,572,441.

(51) Int. Cl.
*A61K 39/395* (2006.01)
(52) U.S. Cl. .................................................. 424/130.1
(58) Field of Classification Search .................. None
See application file for complete search history.

(56) References Cited

U.S. PATENT DOCUMENTS

| | | | |
|---|---|---|---|
| 4,963,367 A | 10/1990 | Ecanow |
| 4,987,127 A | 1/1991 | Sirany |
| 5,629,286 A | 5/1997 | Brewitt |
| 5,683,712 A | 11/1997 | Cavazza |
| 5,698,195 A | 12/1997 | Le et al. |
| 6,136,309 A | 10/2000 | Novick et al. |
| 6,326,360 B1 | 12/2001 | Kanazawa et al. |
| 7,087,726 B2 | 8/2006 | Chuntharapai et al. |
| 7,572,441 B2 | 8/2009 | Epshtein et al. |
| 7,582,294 B2 | 9/2009 | Epshtein et al. |
| 2003/0099636 A1 | 5/2003 | Epshtein et al. |
| 2006/0165697 A1 | 7/2006 | Epshtein et al. |
| 2007/0123518 A1 | 5/2007 | Epshtein |
| 2007/0141058 A1 | 6/2007 | Iliich et al. |

FOREIGN PATENT DOCUMENTS

| | | |
|---|---|---|
| EP | 0652014 A1 | 5/1995 |
| EP | 0687466 A1 | 12/1995 |
| RU | 2007989 C1 | 2/1994 |
| RU | 2033784 C1 | 4/1995 |
| RU | 2104032 C1 | 2/1998 |
| RU | 2122858 C1 | 12/1998 |
| RU | 2137483 C1 | 9/1999 |
| RU | 2144370 C1 | 1/2000 |
| RU | 98109384 A1 | 3/2000 |
| SU | 1730144 | 4/1992 |
| WO | 9412213 A1 | 6/1994 |
| WO | 9422846 | 10/1994 |
| WO | 0105371 A1 | 1/2001 |
| WO | 03055518 A1 | 7/2003 |
| WO | 03037372 A1 | 8/2003 |
| WO | 03077946 A1 | 9/2003 |
| WO | 2008097132 A1 | 8/2008 |
| WO | 2008097133 A1 | 8/2008 |

OTHER PUBLICATIONS

Alexandrova et al., "An Experience of Application of Potentiated Compounds for Jugulation of Alcohol Abstinent Syndrome and Opiate Abstinent Syndrome," Bull of Siberian Branch of RAMS, No. 1 (91), 1999.
Beregovoy et al., On influence of various Dilutions of Monoclonal Antibodies 5F5-B6 on the Formation of Long-Term Post-Tetanic Potentiation in Survived Hippocampal Slices, Bull of Siberian Branch of RAMS No. 1 (91), 1999.
Davenas et al., Nature, 1988, 333: 816-818.
Epshtein et al. May 1999, Bulletin of Experimental Biology and Medicine,vol. 5: 493-495.
Frimel, G., ed., "Immunological Methods," Medicina Publishing House, 1987, pp. 9-33.
Gaevy, M.D. et al., "Osnovy klinicheskoi farmakologii I farmakoterapii," Moscow, Aliyans-B, 2002, pp. 42-44.
Goldacre (2007) Lancet 370: 1672-1673.
Grigoriev M. Yu. et al., "K probleme ispolzovaniya potentsirovannykh organnykh preparatov, " Lechebno-profilakticheskaja Rabota Dlya Meditsinskikh Organizatsij V Ugolnoj Promyshlennosti, vyp. 8, 1989, izd. Tsniehi ugol (Moscow), pp. 163-165.
International Search Report from International Application No. PCT/RU02/00367, filed Aug. 2, 2002, mailed on Dec. 19, 2002.
International Search Report from International Application No. PCT/RU01/00239, filed Jun. 19, 2001, mailed on Sep. 20, 2001.
International Search Report from International Application No. PCT/RU02/00365, filed Aug. 2, 2002, mailed on Dec. 5, 2002.
International Search Report from International Application No. PCT/RU02/00368, filed Aug. 2, 2002, mailed on Dec. 5, 2002.
International Search Report from International Application No. PCT/RU02/00369, filed Aug. 2, 2002, mailed on Dec. 19, 2002.
International Search Report from International Application No. PCT/RU97/00026, filed Feb. 10, 1997, mailed on Apr. 8, 1997.
Ivaniushkin, A. Ja., "Gomeopatiya i sovremennaya meditsina," Vestnik Akademii Meditsinskikh Nauk SSSR, 4, 1988, izd. "Meditsina" (Moscow), pp. 76-82.
Janeway et al. Immunobiology, 1997, 3rd edition, Garland Publishing Inc., pp. 3:1-3:11.
Jeger, J., Ed., "Clinical Immunology and Allergology" (Russian Translation), Meditsina, Moscow, 2000, pp. 358-359.

(Continued)

*Primary Examiner* — Ilia Ouspenski
(74) *Attorney, Agent, or Firm* — Gilman Pergament LLP

(57) ABSTRACT

A medicament based on antibodies contains an activated form of monoclonal, polyclonal, or natural antibodies to interferon in low or ultra-low doses prepared by multiple consecutive dilutions and exposure to external factors, preferably in accordance with homeopathic technology. In order to obtain antibodies, human or heterologous interferon alpha, beta, or gamma, including recombinant interferon, is used; a mixture of various, mostly centimal, homeopathic dilutions being employed. A method of treating a pathologic syndrome, whose formation is affected by interferon, consists in the use of activated forms of antibodies to interferon alpha, beta, or gamma in low or ultra-low doses obtained by multiple consecutive dilutions and exposure to external factors.

5 Claims, No Drawings

OTHER PUBLICATIONS

Kuznik, R.I. et al., "Cytomedines and their Role in Regulation of Physiological Functions," Uspekhi Sovremennoi Biologii, 1995, vol. 115, No. 3, pp. 353-367.

Linde et al., 1997, Lancet, vol. 350: 834-43.

Maini, R. N. et al., "Anti-Cytokine Therapy for Rheumatoid Arthritis," Annu, Rev. Med., 2000; 51: 207-229.

Palace et al., 2003, J. Neur. Sci. vol. 206: 131-134.

Register of Pharmaceuticals of Russia, Encyclopedia of Pharmaceuticals (in Russian), Moscow, 2000, pp. 358-359.

Register of Pharmaceuticals of Russia, Encyclopedia of Pharmaceuticals (in Russian), Moscow, 2001, pp. 788-789.

Schwab, V., "Homeopathic Pharmaceutical Agents. A manual on description and preparation," Moscow, 1967, pp. 12-38.

Shang et al., 2005, Lancet, vol. 366: 726-32.

Skurkovich, et al. Multiple Sclerosis 7:277-284, 2001 "Randomized study of antibodies to IFN-g and TNF-a in secondary progressive multiple sclerosis."

Stefani, D. V. et al., "Immunologiya i immunopatologiya detskogo vozrasta," Moscow, Meditsina, 1996, pp. 28, 29, 358-359.

Vasiliev, Yu, V. et al., "Gomeopatiya: vozrozhdenie traditsionnioy meditsinskoj shkoly," Vestnik Rossijkoj Akademii Nauk, 10, 1992, izd. "Nauka" (Moscow), pp. 145-148.

Vyazov, O.L., Laboratory Methods of Studies in Non-Infection Immunology (in Russian)m Moscow, Meditsina, 1968.

Schwabe, W., "German Homeopathic pharmacopoeia (Homeopathisches Arzneibuch)," Stuttgart, Translation of the 5th Supplement (1991) to the 1978 edition.

MEDICAMENT AND A METHOD OF TREATING A PATHOLOGICAL SYNDROME

This application claims priority of U.S. patent application Ser. No. 10/522,652, filed on Jan. 22, 2005 which is a National Stage under 35 U.S.C. §371 of PCT/RU2002/00369 filed Feb. 8, 2002.

FIELD OF THE INVENTION

The preset invention relates to the field of medicine and can be used for the treatment and prevention of acute and chronic infectious diseases, mostly of viral etiology, and for producing an immunomodulating effect.

BACKGROUND OF THE INVENTION

It is a well-known practice to use antibodies for the treatment of pathologic syndromes (SU 1331598 A, A 61 K 39/00, 1984; SU 1730144 A1, C 12 N 7/00, 1992).

Pharmaceutical preparations (sera, immunoglobulins) based on antibodies employed in therapeutic doses are also well known (see, for instance, Register of Pharmaceuticals in Russia, Encyclopedia of Pharmaceuticals (in Russian), Moscow, 2000, pp. 358-359).

However, the use of such preparations may be accompanied by undesired side effects caused by the injection of substantial doses of foreign proteins into the body.

A method of the treatment of a pathologic syndrome (whose development is affected by various forms of interferon) by the administration of interferon has been described (see, for instance, J. Jeger, Ed., Clinical Immunology and Allergology (Russian translation), Meditsina, Moscow, 1990, Vol. 3, pp. 479-482).

DESCRIPTION OF THE INVENTION

The present invention is directed at obtaining an efficient and safe preparation with immunotropic activity and no tolerance formation by using activated forms of antibodies.

The formulated objective is attained by making an agent containing an activated (potentised) form of monoclonal, polyclonal, or natural antibodies to interferon in low or ultra-low doses prepared by multiple consecutive dilutions and by exposure to external impact, mostly following homeopathic technology.

After the activation (potentiation) of antibodies to interferon the ultra-diluted solutions (or pharmaceutical carriers impregnated with the activated antibodies) retain their biological (pharmaceutical) activity manifested in modification of molecular-cellular and systemic effects mediated by interferon or its receptors. Unlike the action of physiologic (non-activated) forms of antibodies to interferon there is no suppression of the activity of interferon.

The antibodies are obtained with the use of human or heterologous interferon alpha, beta, or gamma, including recombinant interferon.

The agent prepared according to the present invention is a new immunotropic pharmacologic preparation possessing pronounced specific pharmacologic activity, free of side effects, retention of therapeutic action, environmental purity, and low manufacturing costs. In contrast to non-activated forms of antibodies used, among other forms, in small doses, the homeopathically activated (potentised) antibodies to interferon feature an action that does not suppress the activity of endogenous interferon; the activated antibodies act more often synergistically (unidirectionally) with interferon and enhance, among other things, the induction of various forms of endogenous interferon.

It is preferred to use mixtures of different, mostly centimal, homeopathic dilutions.

The method of treating a pathologic syndrome, whose formation mechanisms are affected by interferon, consists in that activated forms of ultra-low doses of antibodies to interferon alpha, beta, or gamma prepared by multiple consecutive dilutions and exposure to external impact are used.

EMBODIMENTS OF THE INVENTION

The new medicament is mainly prepared in the following manner.

Recombinant interferon gamma expressed in the *Escherichia coli* culture is purified by electrophoresis to at least 97% of the active substance and used as an immunogen in hybridoma technology for obtaining monoclonal antibodies. The latter are affinity purified by chromatography on Protein A.

The method of preparation of monoclonal antibodies is described, for instance, in the book edited by G. Frimel, Ed., Immunological Methods, Moscow, Meditsina, 1987, pp. 9-33.

The isolated antibodies to the recombinant human interferon gamma are subjected to consecutive multiple dilutions and to the impact of an external mechanical factor until ultra-low or low doses are obtained, for example, by the homeopathic potentisation procedure (see W. Schwabe, Homöpathisches Arzneibuch, Stuttgart, 1978). This procedure gives rise to a uniform decrease in the concentration through consecutive dilutions of 1 volumetric part of the initial matter (antibodies) in 9 volumetric parts (for decimal dilution, D) or in 99 volumetric parts (for centimal dilution, C) of a neutral solvent with multiple vertical shaking of each solution; preferably, different containers for each subsequent dilution are used. Finally, this procedure gives the required dose (potency).

The external treatment in the course of concentration reduction can also be executed by exposure to ultrasonic, electromagnetic, or other physical factors.

The resultant medicines are used mostly in the dosage forms and dilutions adopted in the homeopathic practice: as alcoholic and aqueous solutions or as tablets (granules) prepared by impregnating the carrier contained in the dosage form by the potentised solution to saturation; also, the potentised solution can be added directly to a liquid dosage form.

Example 1

In studies of the action of antibodies to interferon on the humoral immune response we immunized mice by ram erythrocytes (thymus-dependent corpuscular antigen). After that, the mice received per os a preparation containing homeopathically potentised polyclonal sheep antibodies to murine interferon alpha (a-IFN) in a mixture of C12+C30 dilutions within a period of 5 days. On the first day of the 5-day course the mice also received single intraperitoneal injections of cyclophosphamide (½ of the maximal tolerable dose). Five days later an evaluation of the humoral immune response parameters showed that the administration of potentised antibodies to a-IFN favored the growth of the functional activity of antibody-forming cells in the spleen and an increase in the titres of hemagglutinins in the blood serum, which was particularly important against the background of immunosuppression. Thus, the claimed agent stimulates the humoral immune response.

Example 2

In studies of the action of activated forms of ultra-low doses of antibodies to interferon on the manifestation of the delayed-type hypersensitivity reaction (DHR) of mice we immunized the animals by subcutaneous injection of ram erythrocytes (RE); the challenging dose of RE was injected into the cushion of the rear paw at the end of a 10 days' course of peroral administration of a preparation containing homeopathically potentised monoclonal antibodies (AB) to the murine interferon beta (β-IFN) in a mixture of C12+C30+C200 dilutions in an amount of 0.2 ml.

Simultaneously, we injected saline into the contralateral paw in the same volume. The intensity of the response was assessed 24 hours later from the reaction index (RI), which was calculated individually for each animal from the formula:

$$RI(\%) = (P_o - P_c)/P_c \times 100$$

where $P_o$ is the weight of the test paw, $P_c$ is the weight of the control paw.

Table 1 presents the experimental data.

TABLE 1

Effect of Potentised AB to β-IFN on the Intensity of the DHR

| Indices | Test groups | |
|---|---|---|
| | RE | AB to β-IFN + RE |
| DHR RI | 28.00 ± 2.34 | 36.60 ± 2.00 $P_{cl} = 0.026$ |

It follows that AB to β-IPN activate the function of T-effectors, which is manifested in the enhancement of the delayed-type hypersensitivity reaction in response to sensitization by ram erythrocytes.

Example 3

In studies of the action of activated forms of ultra-low doses of antibodies to interferon on the phagocytal activity of neutrophils in the peritoneal exudate we evaluated the phagocytal activity of neutrophils 24 hours after the end of a 10 days' course of subcutaneous administration of natural antibodies (AB) to interferon gamma (γ-IFN) in a C60 homeopathic dilution in an amount of 0.1 ml.

The phagocytal activity was evaluated from the capacity of these cells to absorb daily culture of St. aureus, Strain 209 (the concentration of the suspension of the microorganisms was $100 \times 10^6$/ml. We took account of the neutrophils that had had absorbed the microorganisms (the phagocytal index, PI) and the average number of staphylococci absorbed by one cell (the phagocytal number, PN).

TABLE 2

Effect of AB to γ-IFN on the Phagocytal Activity of Neutrophils

| Indices | Test groups | |
|---|---|---|
| | RE | AB to γ-IFN |
| PI, % | 8.80 ± 1.36* | 29.20 ± 3.20 $P_{cl} = 0.0004$ |
| PN | 7.61 ± 1.24 | 8.78 ± 2.33 |

These results indicate that AB to γ-IFN stimulate phagocytosis substantially as compared with the control (RE immunization) because of an increase in the proportion of neutrophils capable of absorbing staphylococci.

Example 4

Patient K. (female), aged 62, had been suffering from repeated fits of fever accompanied by eruptions on the chest and pain along the intercostal nerves. Diagnosis: 'relapsing herpes zoster'. The generally adopted therapy (antiviral agents, analgetics) did not bring stable results. As a result of everyday intake of potentised monoclonal antibodies to the human interferon gamma (C 1000, 1 tablet, twice a day), the fever and pain syndrome were arrested on the third day. On the seventh day of the treatment the eruptions virtually disappeared. Recommendation: a preventive intake of the remedy, 1 tablet every other day. No relapses of herpes have been noted within a year.

Example 5

Patient Sh. (male), aged 5, had been regularly examined because of relapsing infections of the upper respiratory tract (rhinolaryngotracheitis lasting 10 days every 2 months). The assessment of his immune status revealed the lowering of the count of CD4 lymphocytes, neutrophils, and interferon gamma in the peripheral blood. Prescription: potentised polyclonal (immune) antibodies to the recombinant human interferon gamma in a mixture of D24+C30+C200 dilutions, 1 tablet every day. Within a period of four months the child had no relapses of acute respiratory infection; his parents say that the child became more active and regained weight. The second evaluation of the immune status 6 months after the beginning of the treatment indicated the normalization of the indices of the cellular and humoral immunity.

Example 6

Patient P. (male), aged 34, complained of rhinitis, pain in the nasopharinx, and subfebrile condition. Diagnosis: acute viral respiratory infection. The intranasal administration of drops of a potentised C12 aqueous solution of monoclonal antibodies to recombinant human interferon gamma (3 times a day) normalized patient's condition within 2 days. A new examination revealed no catarrhal phenomena.

Example 7

Patient S. (male), aged 32, was hospitalized in the infectious unit on the second day of the disease with the diagnosis "influenza with a grave course". Later on, the diagnosis was confirmed virologically. The condition on entry was grave, hyperthermia (up to 41.6° C.), mental confusion, heavy breathing, dry cough. Auscultation revealed vesicular breathing in the lungs. Prescription: monoclonal antibodies to the human interferon gamma in mixed C12+C30+C200 potences, 1 ml of an aqueous solution subcutaneously every 2 hours. Within 6 hours the body temperature fell to 37.4° C., the general condition became satisfactory. During subsequent 3 days the patient received the preparation twice a day, parenterally (1 ml of an aqueous solution). On the fourth day of the therapy the condition was satisfactory, the body temperature was 36.4° C.; the patient noted general weakness. The patient was discharged in a satisfactory condition on the fifth day after hospitalization.

Example 8

Patient U. (male), aged 27, appealed to the urologist with complaints about unpleasant sensations, itch, pain in the urethra, frequent micturate urges, mucosal discharge of one-month duration. A detailed inquiry also revealed pain in the ankles and muco-purulent discharge from the eyes. A visual examination detected hyperemia, edema, and adhesion of the urethral lips. Laboratory immunofluorescence studies of the urethral discharge detected *Chlamidia trachomatis*. Prescription: a mixture of polyclonal antibodies to the human interferons alpha and gamma in a C 1000 homeopathic dilution, 1 tablet every day over a period of 2 weeks. On the fifth day of the treatment the patient noted a pronounced improvement of the symptoms and the lessening of the discharge from the urethra and eyes. At the end of therapy the immunofluorescent analysis of the prostatic secretion for *Chlamidia trachomatis* gave a negative result. Recommendation: administration of the preparation every other day over a period of two weeks. The second examination showed that the patient had no complaints; no signs of the frontal urethritis were found.

The invention claimed is:

1. A medicament comprising a homeopathically potentised form of at least one monoclonal, polyclonal, or natural antibody to alpha or beta interferon wherein said homeopathically potentised form does not suppress the activity of the interferon.

2. The medicament of claim 1, wherein said interferon is human interferon.

3. The medicament of claim 1, wherein said interferon is a recombinant interferon.

4. The medicament of claim 1, wherein said homeopathically potentised form of monoclonal, polyclonal or natural antibody comprises at least one homeopathic dilution.

5. The medicament according to claim 4, wherein said at least one homeopathic dilution comprises one or more centesimal homeopathic dilutions.

* * * * *